United States Patent [19]
Lin et al.

[11] Patent Number: 4,778,469
[45] Date of Patent: Oct. 18, 1988

[54] METHOD OF FORMING TISSUE INGROWTH SURFACE ON SURGICAL IMPLANTS

[75] Inventors: Ruey Y. Lin, New City, N.Y.; Casper F. Stark, Pompton Lakes, N.J.

[73] Assignee: Pfizer Hospital Products Group Inc., New York, N.Y.

[21] Appl. No.: 926,702

[22] Filed: Nov. 4, 1986

[51] Int. Cl.[4] .................... A61F 2/30; A61F 2/32; B29C 33/40
[52] U.S. Cl. ............................. 623/16; 623/1; 623/13; 623/20; 623/22; 623/23; 264/221; 264/293; 264/317; 156/153; 156/155; 156/245
[58] Field of Search .............. 264/1.9, 221, 222, 248, 264/293, 317, 344, DIG. 30, DIG. 44; 156/153, 155, 245, 630; 623/16, 22, 23, 13, 18, 20, 1

[56] References Cited
U.S. PATENT DOCUMENTS

| | | | |
|---|---|---|---|
| 4,439,391 | 5/1984 | Hung | 264/293 |
| 4,473,421 | 9/1984 | Gustafsson | 264/DIG. 30 |
| 4,613,393 | 9/1986 | Cattanach et al. | 156/155 |
| 4,644,942 | 2/1987 | Sump | 623/16 |
| 4,656,094 | 4/1987 | Kojima et al. | 264/176.1 |
| 4,657,544 | 4/1987 | Pinchuk | 623/1 |

FOREIGN PATENT DOCUMENTS 2142830  1/1985  United Kingdom ............ 623/16

*Primary Examiner*—Michael S. Marcus
*Assistant Examiner*—Richard D. Jordan
*Attorney, Agent, or Firm*—Peter C. Richardson; Lawrence C. Akers; Mark Dryer

[57] ABSTRACT

A method of producing a site for tissue ingrowth on a surgical implant by embedding a space occupier possessing a desired pattern in the surface of the implant at the desired location for ingrowth and then solubilizing the embedded space occupier to leave the pattern on the implant surface. Preferably, the implant is fabricated from a composite comprising a semi-crystalline thermoplastic resin such as polyetheretherketone or polyphenylene sulfide, and the space occupier is an acid-soluble metal plate machined to produce the desired pattern and removed by aqueous acid solution.

13 Claims, 1 Drawing Sheet

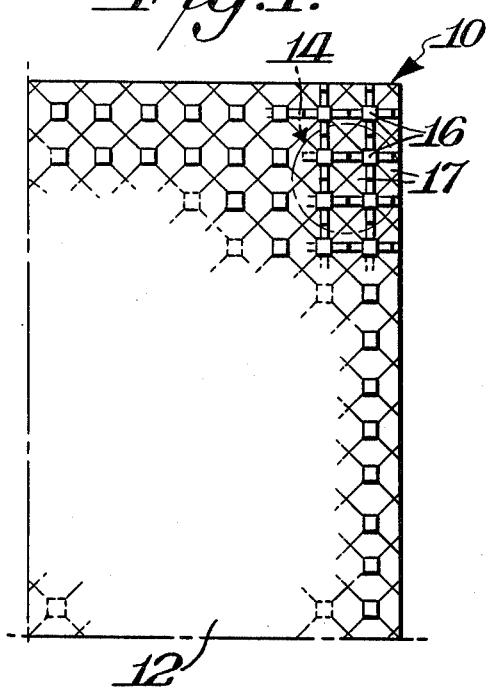
Fig. 1.
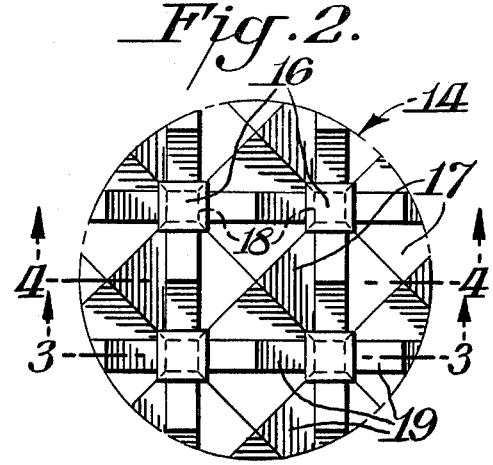
Fig. 2.
Fig. 3.
Fig. 4.
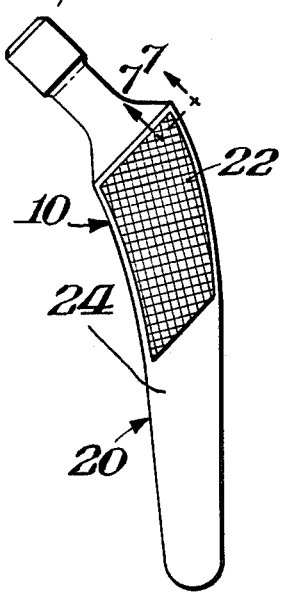
Fig. 5.
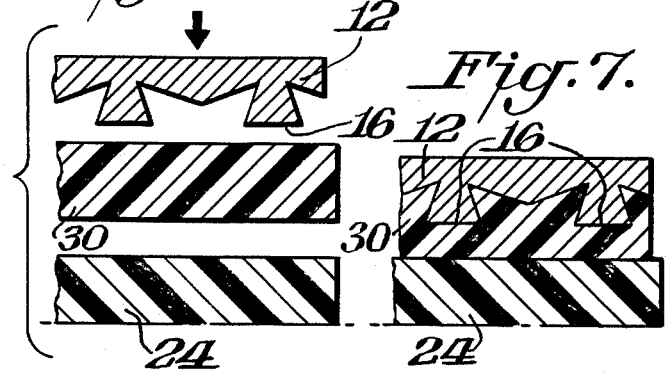
Fig. 6.
Fig. 7.
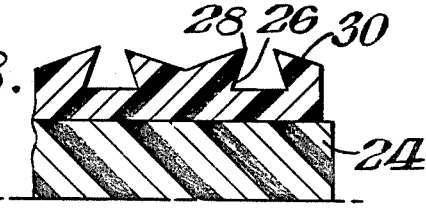
Fig. 8.

METHOD OF FORMING TISSUE INGROWTH SURFACE ON SURGICAL IMPLANTS

BACKGROUND OF THE INVENTION

This invention concerns a method of producing tissue ingrowth surface on surgical implants.

Until recently, most surgical implants such as prosthetic hip stems were implanted with the aid of bone cement to provide fixation of the implant in its desired location. With such fixation, however, the implant may tend to work loose from the cement, possibly causing failure of the implant or pain and discomfort to the patient. Alternative means of implant fixation have therefore been attempted.

One alternative to cement fixation is the use of certain textures on selected areas of the implant surface to produce tissue ingrowth into these areas and therefore stabilization of the implant. Several patterns for such texturized surfaces can be found in existing metal alloy prosthetic devices. These patterns cannot, however, be readily formed on the surface of polymeric devices by presently employed techniques because of the difference in material properties of, and processing methods employed with, polymeric substances.

It is therefore the primary objective of the present invention to provide a simple and inexpensive means for preparing desired texturized surfaces on body implants made from polymeric composites or other material systems.

SUMMARY OF THE INVENTION

This objective is realized with the present method of producing tissue ingrowth sites on a surgical implant, which comprises the steps of embedding a space occupier possessing a desired pattern for tissue ingrowth in the surface of the implant at a selected portion of the implant where tissue ingrowth is desired, then solublilizing the embedded space occupier with an agent nonreactive toward the implant to leave the desired pattern on the implant surface.

The space occupier is preferably in the form of an acid-soluble metal plate, suitably fabricated from aluminum or zinc and machined to obtain the desired pattern, which is solubilized with an aqueous acid solution, or in the form of particulate water-soluble inorganic salt which is solublized with water.

In other preferred embodiments, the space occupier is pressed into the implant surface, in which case the implant surface at the selected portion may be fabricated of a material which penetrates into undercuts in the space occupier more readily than that of the bulk of the implant, the material preferably being in the form of a sheet which fuses with the implant; the implant is fabricated from a composite comprising a thermoplastic resin, especially a semi-crystalline thermoplastic resin such as a polyetheretherketone or polyphenylene sulfide; and the implant is a joint prosthesis, especially a prosthetic hip stem.

The present invention also contemplates a surgical implant having tissue ingrowth surface produced by the above method.

BRIEF DESCRIPTION OF THE DRAWINGS

The features and advantages of the present invention will become apparent from the following detailed description and the accompanying drawings, in which:

FIG. 1 is a top plan view of a space occupier of the present invention in the form of a metal plate having a machined pattern on its upper surface for transfer to a surgical implant;

FIG. 2 is an enlarged top plan view of a portion of the pattern shown in FIG. 1;

FIG. 3 is an enlarged cross-sectional view of a portion of the plate taken along the line 3—3 of FIG. 2;

FIG. 4 is an enlarged cross-sectional view of a portion of the plate taken along the line 4—4 of FIG. 2;

FIG. 5 is a side elevational view of a hip stem prosthesis showing the texturized pattern of the plate of FIG. 1 transferred to a selected portion of the proximal region of the stem;

FIG. 6 is an enlarged cross-sectional view showing the patterned plate before being embedded in the prosthesis surface;

FIG. 7 is an enlarged cross-sectional view taken along the line 7—7 of FIG. 5 showing the patterned plate embedded in the prosthesis surface; and FIG. 8 is an enlarged cross-sectional view showing the embedded patterned plate of FIG. 7 solubilized, resulting in a pattern transferred to the prosthesis.

DETAILED DESCRIPTION OF THE INVENTION

The method of the present invention provides a simple and economical means for producing complex texturized fixation patterns on surgical implants, made of polymeric composites or other material systems, in a controlled and reproducible manner, such patterns often being impossible to produce by existing techniques.

The desired fixation pattern on the implant is readily established by the shaping or machining of the removable space occupier, and since the pattern is created in the implant material itself, the potential problem of weakening at the boundary of the fixation phase and the implant material encountered with certain present methods, such as those for prostheses having sintered metal implant surfaces, does not exist.

Such a fixation pattern is shown in FIGS. 1-4 of the drawings. Here the space occupier is a machined, acid-soluble plate 10 fabricated of such as aluminum or zinc. By space occupier is meant a substance nonreactive with the material of construction of a surgical implant and possessing a pattern which is desired to be transferred to a selected surface of the implant by embedding the substance with its pattern in that surface and then solubilizing the substance with an agent which does not react with the implant, thereby leaving the desired pattern on the surface of the implant.

Plate 10 has a surface 12 with the repeat pattern 14 shown in FIG. 2. Pattern 14 includes tapered posts 16 with undercuts 18 as well as pyramids 17 and triangular ridges 19, as shown in FIGS. 3 and 4. Plate 10 may be fabricated of any material in which the desired pattern for the texturized surface of an implant may be formed and with which the implant is compatible or nonreactive. Likewise, the solubilizing agent for the plate may be any substance which will solubilize and remove the plate without reacting with or otherwise affecting the implant to thereby leave the transferred pattern intact in the implant surface. For example, when the implant is fabricated from such semi-crystalline thermoplastic polymers as polyetheretherketone (PEEK) or polyphenylene sulfide (PPS), with or without carbon fiber reinforcement, the plate may be fabricated from such as aluminum and solubilized with aqueous hydrochloric acid or sodium hydroxide; zinc and solubilized with aqueous hydrochloric acid; or silver and solubilized with aqueous nitric acid.

When pattern 14 is to be transferred to a body implant, such as prosthetic hip stem 20 shown in FIG. 5, a portion of plate 10 is cut to a desired shape and size, such as area 22, and then embedded in the surface 24 of stem 20. If stem 20 is fabricated from a thermoplastic resin such as PEEK or PPS, plate 10 may be pressed into stem 20 by such as compression molding at a temperature at or above the softening point of the resin. Embedded plate 10 is then solubilized with such as dilute aqueous hydrochloric acid to leave a texturized surface on stem 20 having a profile as shown in FIG. 8. Now the upper edge of tapered post 16 of plate 10 has become undercut 26 of stem 20 while undercut 18 of plate 10 has become ridge 28 of stem 20.

In a preferred embodiment of the present method, as shown in FIGS. 6-8, intermediate sheet 30 is placed between plate 10 and surface 24 in area 22 prior to embedding plate 10. Sheet 30 is fabricated of a material which fuses to surface 24 and penetrates into undercuts 18 of pattern 14 more readily than the material of surface 24 and the bulk of stem 20. This insures that undercuts 26 and ridges 28 of the texturized surface on area 22 are well defined, and at the same time avoids a discontinuity between the fixation surface and the bulk of stem 20. Thus, for example, implant 20 may be fabricated of a PEEK prepreg containing 60 weight percent unidirectional carbon fibers to provide a strong stem prosthesis while sheet 30 may be fabricated from PEEK containing up to 30 weight percent chopped carbon fiber pellets to insure a well defined tissue ingrowth area 22 on the prosthesis which is integral with stem 20.

In additon to machined or molded plates to form machine fixation patterns, other space occupiers may be used. For example, the space occupier may be in the form of an inorganic salt of a particular crystal shape or size which is solubilized by water. Thus sodium chloride powder may be used to produce a fine indentation on the implant surface, while cubic sodium chloride crystals will produce cube valleys. Marble chips solubilized by dilute aqueous acid will produce irregular surface indentations. The previously mentioned metals, in addition to being in machined or molded plate form, may also be used to produce other patterns. For example, aluminum chips may be used to form irregular surface indentations, while aluminum beads will produce regular spherical indentations of controlled diameter and depth.

The implant material itself need only be capable of being embedded by the space occupier and inert to both the space occupier and the solubilizing agent. Thus, in additon to the semi-crystalline thermoplastic resins mentioned above, the implant material, for example, may be other thermoplastic resins such as polyethylene and polypropylene; thermosetting resins such as epoxy and phenol-formaldehydes; ceramics such as hydroxyapatite; pyrolytic carbon; and metals such as Vitallium ® or titanium. Those skilled in the art will be able to select the proper combination of implant material, space occupier and solubilizing agent.

The following examples are merely illustrative and should not be construed as limiting the invention, the scope of which is defined solely by the claims.

EXAMPLE 1

A 30 mil (0.8 mm) sheet prepared by compression molding a composite mixture of 30 weight percent chopped carbon fiber pellets (CCF)[1] in a polyetheretherketone (PEEK) matrix was placed between an aluminum plate having on its lower surface a premachined pattern as shown in FIGS. 1-4 and a 5 mm layer of a composite substrate of 60 weight percent carbon fibers (CF) in PEEK[2]. The resulting stack was placed in a mold for compression molding at 720° F. (382° C.). When the stack reached the temperature at which the PEEK resin was in a molten state, a compression pressure of about 100 psi (6.8 atm) was applied to laminate the intermediate PEEK/CCF sheet to the PEEK/CF substrate and embed the machined pattern of the aluminum plate in the laminate surface, as shown in FIG. 7.
(1) 450CA30 pellets, ICI, Wilmington, Del.
(2) APC-2 prepreg, ICI The laminate with embedded aluminum plate was cooled to room temperature and dipped into a 3N aqueous hydrochloric acid solution to solubilize the aluminum plate, leaving a composite plaque with a textured surface having a clean, orderly pattern the inverse of that of the original aluminum plate, as shown in FIG. 8.

EXAMPLE 2

The procedure of Example 1 was repeated with the exception that the intermediate sheet was prepared by compression molding a composite of 30 weight percent CCF[1] in polyphenylene sulfide (PPS) resin; the substrate layer was a composite prepared from PPS/CF prepreg containing 60 weight percent unidirectional carbon fibers[2]; and the stack was compression molded at 600° F. (316° C.). A composite plaque with a clean, orderly texturized surface was again obtained.
(1) AC 50-30 pellets, Phillips Petroleum Company, Bartlesville, Okla.
(2) PPS/CF prepreg, Phillips Petroleum Company Similar results were realized when a premachined zinc plate was substituted for the aluminum plate.

EXAMPLE 3

A PEEK/CF composite hip stem of the style shown in FIG. 5 was prepared by compression molding. The aluminum plate and intermediate PEEK/CCF sheet employed in Example 1 were cut to the size of and placed over the area of the stem intended for tissue ingrowth as shown by numeral 22 in FIG. 5. The stem with attached intermediate sheet and machined plate was returned to its mold and recompression molded at 720° F. The recompressed stem was cooled, removed from the mold, and dipped into 3N aqueous hydrochloric acid to solubilize the embedded aluminum plate. The resulting stem had a texturized tissue ingrowth area with a cross-section profile as shown in FIG. 8.

EXAMPLE 4

Aluminum beads of 1 mm diameter, a 30 mil sheet of PEEK resin and a 5 mm thick PEEK/CF composite substrate were stacked, and the stack compression molded and then acid treated to solubilize the embedded aluminum beads as in Example 1. A composite plaque with holes for tissue ingrowth evenly distributed on its surface was produced, the holes representing the space occupied by the embedded aluminum beads.

Substitution of aluminum chips for the aluminum beads resulted in a composite plaque with a textured surface of irregular shaped depressions, while use of aluminum foam resulted in a composite plaque with surface texture and undercut channel structure created by the imbedded foam.

While the above description and examples have been directed primarily to a hip stem prosthesis, the method of the present invention may also be employed with other prosthetic devices, such as acetabular cups and knee joints, as well as with other surgical implants, including cardiovascular implants, ligaments and tendons, which profit from tissue ingrowth surface.

We claim:

1. A method of producing a site for tissue ingrowth on a surgical implant, which comprises the steps of:
    embedding a space occupier possessing a desired pattern for tissue ingrowth directly into the surface of the implant by pressing the space occupier directly into the implant surface at a selected portion of the implant where tissue growth is desired; and
    solubilizing the embedded space occupier with an agent non-reactive toward the implant to remove the space occupier and leave the desired pattern of sufficient depth in the implant surface to accept tissue ingrowth.

2. The method of claim 1 wherein the space occupier is in the form of an acid-soluble metal plate with a surface containing the desired pattern, and the solubilizing agent is an aqueous acid solution.

3. The method of claim 2 wherein the plate surface is a machined surface.

4. The method of claim 2 wherein the metal plate is fabricated from aluminum or zinc.

5. The method of claim 1 wherein the space occupier is in the form of particulate water-soluble inorganic salt, and the solubilizing agent is water.

6. The method of claim 1 wherein the implant surface at the selected portion is fabricated of a material which penetrates into undercuts in the space occupier more readily than that of the bulk of the implant.

7. The method of claim 6 wherein the material is in the form of a sheet which fuses with the implant.

8. The method of claim 1 wherein the implant is fabricated from a composite comprising a thermoplastic resin.

9. The method of claim 8 wherein the thermoplastic resin is semi-crystalline.

10. The method of claim 9 wherein the thermoplastic resin is a polyetheretherketone or polyphenylene sulfide.

11. The method of claim 1 wherein the implant is a joint prosthesis.

12. The method of claim 11 wherein the joint prosthesis is a hip stem.

13. A surgical implant having tissue ingrowth surface produced by the method of claim 1.

* * * * *